United States Patent
Berguer et al.

(10) Patent No.: US 9,681,915 B2
(45) Date of Patent: Jun. 20, 2017

(54) SEPTOTOMY CATHETER FOR AORTIC DISSECTION

(71) Applicants: Ramon Berguer, West Bloomfield, MI (US); Juan Parodi, Miami, FL (US)

(72) Inventors: Ramon Berguer, West Bloomfield, MI (US); Juan Parodi, Miami, FL (US)

(*) Notice: Subject to any disclaimer, the term of this patent is extended or adjusted under 35 U.S.C. 154(b) by 0 days.

(21) Appl. No.: 15/131,504

(22) Filed: Apr. 18, 2016

(65) Prior Publication Data

US 2016/0228181 A1    Aug. 11, 2016

Related U.S. Application Data

(63) Continuation-in-part of application No. 14/591,642, filed on Jan. 7, 2015, now abandoned.

(Continued)

(51) Int. Cl.
*A61B 18/14*    (2006.01)
*A61B 18/24*    (2006.01)
(Continued)

(52) U.S. Cl.
CPC .. *A61B 18/1492* (2013.01); *A61B 17/320016* (2013.01); *A61B 18/1445* (2013.01);
(Continued)

(58) Field of Classification Search
CPC ........ A61B 18/1445; A61B 17/320016; A61B 2018/1452; A61B 2018/144;
(Continued)

(56) References Cited

U.S. PATENT DOCUMENTS 6,036,667 A    3/2000   Manna et al.
2005/0070889 A1*    3/2005   Nobis .............. A61B 17/32001
                                          606/45

(Continued)

FOREIGN PATENT DOCUMENTS

WO    2008019097    12/2008
WO    2014009554    1/2014

OTHER PUBLICATIONS

International Search Report dated Feb. 25, 2016; International Application No. PCT/US2015/061028; International Filing Date: Nov. 17, 2015; 4 pages.

(Continued)

*Primary Examiner* — Katherine M Shi
*Assistant Examiner* — Michael Mendoza
(74) *Attorney, Agent, or Firm* — Blank Rome LLP

(57) ABSTRACT

Medical methods and devices for treating aortic dissections. A catheter-based cutting device permits cutting a septum of acute or chronic aortic dissections, in a retrograde manner. The catheter includes a base section having a central lumen therethrough, two flexible arms extending from a distal end thereof, where each arm has a channel therethrough for a passage of a guide wire. With distal ends of the two flexible arms separated, the two arms form a Y-shape with the base section. With distal ends of the two flexible arms together, the two arms have a longitudinal profile, about a periphery thereof, identical to a longitudinal profile of the base section. A non-mechanically actuated cutting component resides between the two arms in a vicinity of the distal end of the base section. The cutting component faces distally outward between the two arms with the distal ends of the two flexible arms separated.

20 Claims, 4 Drawing Sheets

Related U.S. Application Data

(60) Provisional application No. 62/300,252, filed on Feb. 26, 2016.

(51) Int. Cl.
*A61B 17/32* (2006.01)
*A61B 17/00* (2006.01)
*A61B 18/00* (2006.01)
*A61B 17/3207* (2006.01)
*A61B 17/22* (2006.01)

(52) U.S. Cl.
CPC .......... *A61B 18/24* (2013.01); *A61B 17/3207* (2013.01); *A61B 2017/00292* (2013.01); *A61B 2017/22021* (2013.01); *A61B 2017/22039* (2013.01); *A61B 2017/22068* (2013.01); *A61B 2017/320028* (2013.01); *A61B 2017/320076* (2013.01); *A61B 2018/00345* (2013.01); *A61B 2018/00351* (2013.01); *A61B 2018/00404* (2013.01); *A61B 2018/00601* (2013.01); *A61B 2018/144* (2013.01); *A61B 2018/1412* (2013.01); *A61B 2018/1452* (2013.01)

(58) Field of Classification Search
CPC .. A61B 2018/1412; A61B 2018/00345; A61B 2018/00404; A61B 2018/00351; A61B 2017/320028; A61B 17/3207; A61B 2017/22021; A61B 2017/22039; A61B 2017/22068

See application file for complete search history.

(56) References Cited

U.S. PATENT DOCUMENTS

| | | |
|---|---|---|
| 2010/0125292 A1 | 5/2010 | Wiener et al. |
| 2011/0118769 A1 | 5/2011 | Bliss et al. |
| 2013/0211403 A1 | 8/2013 | Suon et al. |
| 2014/0012252 A1 | 1/2014 | Bliss et al. |

OTHER PUBLICATIONS

Written Opinion dated Feb. 25, 2016; International Application No. PCT/US2015/061028; International Filing Date: Nov. 17, 2015; 7 pages.

* cited by examiner

SEPTOTOMY CATHETER FOR AORTIC DISSECTION

RELATED INVENTIONS

This application is a continuation-in-part of U.S. application Ser. No. 14/591,642, filed Jan. 7, 2015. This application also claims benefit of priority of U.S. Provisional Application Ser. No. 62/300,252, filed Feb. 26, 2016. The above-identified related applications are incorporated herein by reference.

FIELD OF THE INVENTION

The present invention relates to medical methods and devices for treating aortic dissections; and more particularly for safely cutting the septum of an aortic dissection.

BACKGROUND OF THE INVENTION

Aortic dissection is an uncommon but often lethal condition where the inner layer of the aorta separates from the outer layer, creating a double channel. The moving septum thus created disrupts the flow of blood to the legs and viscera. Additionally, the thin outer wall resulting from the delamination of the aorta often develops into an aneurysm that may eventually rupture.

Generally, a dissection starts by a tear involving the inner layer of the aorta that causes the inner layer to separate from the outer layer over part of the circumference of the aorta. Upon dissection, a new channel is formed between the separated outer and inner layers of the blood vessel wall of the aorta. This results in the aorta having two channels instead of one. The inner layer of the blood vessel wall that has separated is called the septum (or the flap) and separates the two channels.

One of the two channels formed in a dissection continues to function as a blood vessel, allowing the blood to flow through it. This channel is called the "true lumen." The newly formed second channel through which blood also flows is called the "false lumen." The true and false lumens communicate proximally through a proximal tear and distally through one or possibly various existing distal tears. In some dissections, there is no distal tear.

A dissection which involves the thoracic aorta is called a "thoracic aortic dissection." There are two types. Type A dissections involve a dissection in the ascending aorta, while type B dissections involve any segment of the descending aorta. Type A dissections require immediate surgery. Management of type B dissections is the subject of controversy. Some doctors advocate temporary medical management, while others advocate immediate stent-grafting. In cases where the septum is blocking an opening of a major artery supplying the viscera or the leg, urgent surgery may be required, and may be limited to a resection of part of the septum (fenestration) providing communication between the true and the false lumens. In a few cases, this needed communication can be achieved by perforating the septum and enlarging the resulting perforation with a balloon (balloon fenestration).

A variation of the balloon fenestration involves inserting and advancing two wires through the false and true lumen to a proximal point, and linking the two wires in some fashion to cut the septum with the resulting wire loop. This variation lacks control of the site and of the length of the tearing maneuver. These attempts have been complicated by anecdotal reports of high pressure of the false lumen channel with collapse of the true lumen and by detachment and folding of the septum, obstructing the outflow of the aorta.

One of the wires should be advanced into the true lumen, the other into the false lumen. Entering the false lumen would be easy if both lumens reach down to the femoral artery puncture site. If the false lumen ends proximal to the femoral artery, the false lumen could be engaged by penetrating the orifice of communication between the true and the false lumen, or by puncturing the septum as distally as possible, inserting a wire in the false lumen and dilating the orifice with a balloon to allow the septotomy cutter to engage the septum at this point. Both wires should come out of the body through the same orifice, either a cut-down in the common femoral artery or a sheath inserted in it.

Catheter based cutting methods and tools for aortic dissections are found in Bliss, US 2011/0118769. Bliss primarily teaches use of a movable cutting blade, where a U-shaped or hooked tool penetrates a septum, then hooks and cuts the septum in a proximal to distal direction by retracting a portion or entirety of the catheter, or by distally translating the cutting blade relative to the septum. The cutting of a septum of a aortic dissection, in a proximal to distal direction, is problematic. This type of cutting, by the pulling of the septum in a distal direction, using a fixed or movable blade, may result in sudden collapse of the true lumen with catastrophic consequences. Safe division of the septum requires distal to proximal cutting.

Bliss does suggest one embodiment of a catheter based cutting device intended to operate in a retrograde manner (i.e., cutting the septum from distal to proximal along the aortic dissection). The embodiment has fixed, passive, cutting blade fashioned from a small, standard surgical knife (razor blade) intended to be pushed proximally against the septum by an inner tubular component (actuator) of the catheter. This passive cutting blade does not permit a controlled septotomy. The actuator acts as a telescopic mechanism by sliding inside an outer tubular component of the catheter. The coaxial catheter system extends the length of the catheter and creates substantial friction during advancement of the catheter within the blood vessel. The friction naturally increases with any increase in diameter of the two tubular components. A catheter with inner and outer tubular components functioning telescopically does not have the flexibility to navigate the bends of the arterial system and, if some bending has been achieved, the friction between the two tubular components would increase dramatically. Further, the embodiment disclosed includes a distal end having a fixed "Y" assembly. A stationary cutting blade (razor blade) is adhered between diverging ends of two tubular components (or fixed arms) in a Y-shape. The resultantly immobile, Y-shaped distal end is a substantially large assembly for introduction into (and maneuverability within) a blood vessel. Further, maneuverability and control of the cutting assembly at the septum, during septum cutting, and the required pushing of a fixed, passive blade against the septum, makes this embodiment inoperable.

What is needed is a catheter based cutting device operable in a retrograde manner, having a cutting assembly and cutting component that controls the site and length of the septum cut in both acute and chronic aortic dissection. In acute dissections, the device would equalize pressure between the true and the false lumens, potentially avoiding development of an aneurysm, as well as correcting malperfusion of the viscera or legs. Acute aortic dissections often require only a few centimeters of septum division to equalize pressure between the lumens, and to provide low resistance outflow of both lumens to avoid development of aneurysmal dilatation of the false lumen (e.g., 5-15 cm in the instance of cutting from the level of the aortic bifurcation to below the renal arteries). In chronic dissections, where different viscera may be perfused by either lumen, a cutting device is needed to convert the double lumen into a single one, where cutting the fibrous septum permits insertion of a branched endograft in a manner similar to that used in thoracoabdominal aneurysms. Also needed is a catheter based cutting device having no mechanical actuator, providing small profile construction, where the cutting component is an electrode or a fiber delivering energy that cuts the septum upon placement, without need for a mechanical push mechanism. As a result, the catheter can have a small diameter and increased flexibility which facilitates advancement of the catheter through a tortuous aorta.

SUMMARY OF THE INVENTION

The present invention solve the problems noted above, providing catheter-based cutting methods and devices operable in a retrograde manner (distal to proximal cutting), that controls the site and length of the septum cut in both acute and chronic aortic dissection. In acute dissection, the present catheter equalizes pressure between the true and false lumens, potentially avoiding the development of an aneurysm, as well as correcting malperfusion of the viscera or legs. In chronic dissections, where different viscera may be perfused by either lumen, the present catheter converts the double lumen into a single one, where cutting the fibrous septum permits insertion of a branched endograft in a manner similar to that used in thoracoabdominal aneurysms. The present catheter has no mechanical actuator and hence can be constructed with small profile. As a result, the present catheter has a small diameter with increased flexibility which facilitates advancement through tortuous aorta.

The catheter of the present invention avoids the need for a mechanical actuator which would need to be operated from the entry point of the catheter to its end, usually about 70-80 cm away, and allows the construction of a cutting catheter with a low profile since it does not need rigid mechanical actuators for the mechanical blade. The present catheter has the flexibility needed to accommodate the curves of the aortic and iliac arteries system. The bifid end of the catheter, when introduced, is collapsed and has the same diameter as the rest of the catheter. The two arms of the catheter only open when the wires that guide them diverge after encountering the lower end of the septum.

The present invention provides catheter-based cutting methods and devices operable to cut the septum of an aortic dissection (septotomy), whether the dissection is acute or chronic. The invention involves a septotomy catheter having a base section with a pair of bifid arms extending from a distal end of the base section. The catheter uses guide wires that extend through and beyond the arms to guide the septotomy catheter such that an area defined by a vertex formed by the two arms and base section of the catheter will engage a septum when the catheter is advanced, in a retrograde manner, in a blood vessel. At the vertex, where an end of the septum is engaged, a cutting component of the catheter cuts the septum as the catheter is proximally advanced using guide wires as essentially parallel rails.

The present invention includes various embodiments. In at least one embodiment, a septotomy catheter is provided that includes a base section having a central lumen therethrough, two flexible arms extending from a distal end of the base section, where each arm has a channel therethrough for a passage of a guide wire. With distal ends of the two flexible arms separated, the two arms form a Y-shape with the base section. With distal ends of the two flexible arms together, the two arms have a longitudinal profile, about a periphery thereof, identical to a longitudinal profile of the base section. The catheter also includes a non-mechanically actuated cutting component residing between the two arms in a vicinity of the distal end of the base section. The cutting component faces distally outward between the two arms with the distal ends of the two flexible arms separated.

In one or more embodiments, the cutting component spans the two flexible arms when the arms are separated. In these embodiments, the cutting component resides perpendicularly to a longitudinal axis of the catheter.

In one or more embodiments, the two flexible arms each further comprise a notch therein, each notch housing a respective end of the cutting component, each notch providing that the respective end of the cutting component is not exposed outside the catheter when the two arms are separated. With distal ends of the two arms together, the catheter completely houses the cutting component therein, whereby no part of the cutting component is exposed outside the catheter.

In one embodiment, the cutting component is an electrode spanning the two flexible arms when separated, residing perpendicularly to a longitudinal axis of the catheter. The electrode is energized by radio-frequency (RF) current. The electrode can be a wire, bar, rod, flat sheet, blade or plate. If a flat sheet, plate or blade, the electrode can be entirely insulated except for a most distal portion thereof which is uninsulated. The insulation can be a medical grade epoxy. The uninsulated portion of the flat sheet, plate or blade, along a distal edge thereof, might resemble a wire or rod, or sharpened tip thin blade. The uninsulated portion spans the two flexible arms when separated, residing perpendicularly to the longitudinal axis of the catheter. If a flat sheet, plate or blade, the longitudinal, insulated sides would reside inside respective notches of the two arms.

The radio-frequency (RF) current can be provided by a wire residing within the central lumen of the base section. The RF energization can be monopolar or bipolar.

In another embodiment, the cutting component of the catheter is laser light generated by an excimer laser. An excimer laser fiber can reside within the central lumen of the base section. The two bifid arms, with distal ends together, completely house the excimer laser fiber therein, whereby no part of the cutting component is exposed outside the catheter. In this embodiment, if notches are included in the two arms, each notch would house, and/or would be configured to provide unrestrained operation of, and laser light emission from, a distal end of the excimer laser fiber, in a vicinity of the base section, when the two arms are separated.

In another embodiment, the cutting component is an ultrasonic cutting blade, having a cutting edge facing distally and spanning the two flexible arms when the arms are separated. An ultrasonic static motor can reside within the base section, along the central lumen thereof. The cutting blade cuts by ultrasound energy and its high frequency vibration can be delivered by a minute piezoelectric ceramic energized through a thin electrical wire passing through the central lumen of the base section.

In still another embodiment, the catheter can further include two base section channels extending through an entirety of the base section. The base section channels are parallel to the central lumen, with each base section channel communicating with a respective channel of the arm to provide passage of two guide wires, one guide wire per channel, through an entirety of the catheter.

A method of treating an aortic dissection is also provided, using an embodiment of the septotomy catheter. The method involves inserting two guide wires into an arterial system. Moving the two guide wires proximally, into a descending aorta, where the two guide wires are substantially parallel to one another and spaced apart a distance. A septum of the aortic dissection is then penetrated, with a first of the two guide wires, into a false lumen of the aortic dissection, distal of a proximal tear of the aortic dissection, at a certain location. At this certain penetration location, the guide wires become more separated from one another. The two guide wires are moved further proximally, toward the proximal tear, with the first guide wire in the false lumen and a second guide wire in a true lumen of the aortic dissection, with septum of the aortic dissection between the two guide wires. The guide wires remain spaced apart, proximal of the certain location of septum penetration, at least the distance or greater;

The method then includes inserting a distal end of the septotomy catheter over the guide wires, one guide wire in each of the two channels of the septotomy catheter. The septotomy catheter is moved proximally in the arterial system, with guide wires passing therethrough, toward the aortic dissection, the septotomy catheter tracking the substantially parallel guide wires and remaining closed, with the distal ends of the arms together, completely housing the cutting component therein, whereby no part of the cutting component is exposed outside the catheter. The septum of the aortic dissection is then penetrated with one of the flexible arms, into the false lumen thereof, at the certain location, while the one of the flexible arms tracks the first guide wire into the false lumen and then proximally thereof and the other of the flexible arms tracks the second guide wire proximally in the true lumen. At the certain location, the distal ends of the two flexible arms separate, forming a Y-shape with the base section to expose the cutting component outside the catheter, from between the flexible arms, with the cutting component facing distally relative to the catheter. The septotomy catheter is moved further proximally, with arms separated. The catheter receives the septum between the separated arms, where the separated arms, with catheter moving proximally, direct a distal end of the septum into the cutting component. The septum is cut a desired distance determined by further proximal movement of the catheter. During the method, the cutting component is energized only upon receipt of the septum between the separated arms, with septum in close proximity to the cutting component.

BRIEF DESCRIPTION OF THE ILLUSTRATED EMBODIMENTS

The present invention will be better understood with reference to the following description taken in combination with the drawings. For the purpose of illustration, there are shown in the drawings certain embodiments of the present invention. In the drawings, like numerals indicate like elements throughout. It should be understood, however, that the invention is not limited to the precise arrangements, dimensions, and instruments shown:

Figure 7:
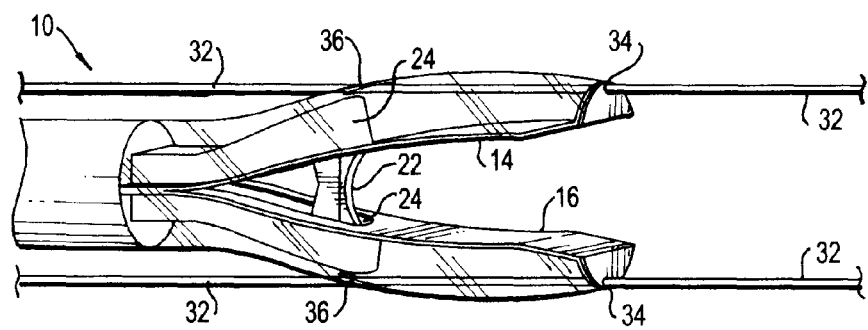
Figure 8:
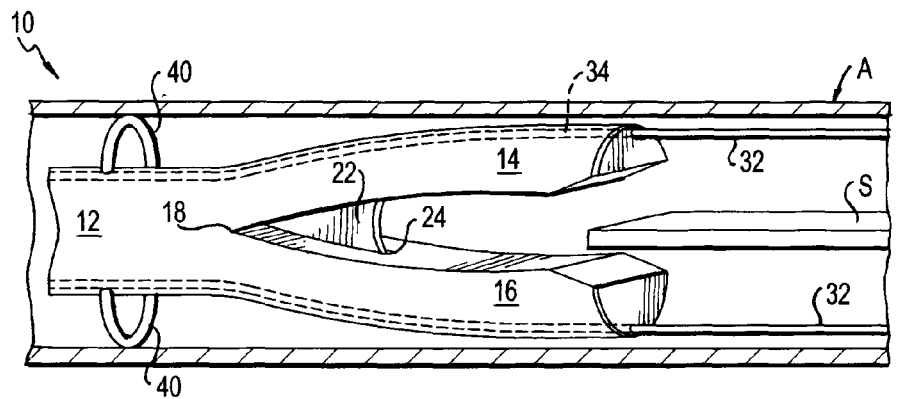

FIG. 7 illustrates an alternative feature of a catheter embodiment of the present invention, and further showing (via see-through arm portions) aspects of the present invention; and FIG. 8 illustrates an alternative feature of a catheter embodiment of the present invention, showing flexible wings extending axially from a base section of the catheter, proximal to the cutting component, to assist alignment of the catheter, and the cutting component, within the aorta and toward a center axis of the septum.

DETAILED DESCRIPTION OF THE ILLUSTRATED EMBODIMENTS

The catheter of the present invention is used for cutting a septum in an aortic dissection, whether acute (where the septum is thin and mobile) or chronic (where the septum is thick and immobile). The catheter can, for instance, be inserted into a dissected aorta in the treatment of Type B thoracic aortic dissections. The figures show the device as described below, and use the same reference numeral for the same element in each drawing. When referring to the catheter of the present invention, an end of the catheter remaining outside the patient is referred to as the proximal end, and an end of the catheter comprising the cutting assembly is referred to as the distal end. When referring to the aortic dissection, the septum thereof, and surgical activity around the septum, an end of the dissection closest to the heart is referred to as the proximal end, and an end furthest from the heart is referred to as the distal end (bottom of page of FIGS. 6 and 7).

Figure 1:
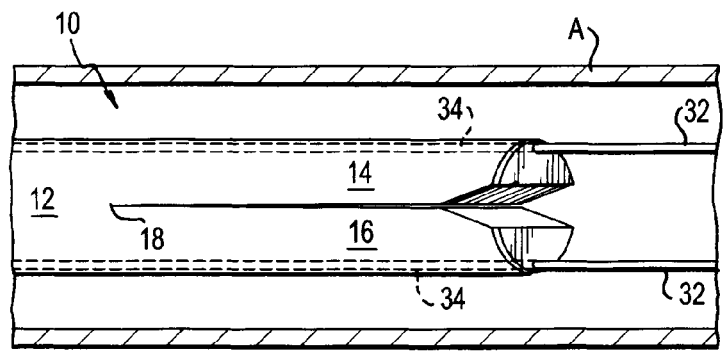
FIG. 1 illustrates a view of a catheter within a blood vessel (the blood vessel shown in section), the catheter traversing over guidewires and shown in a closed, non-cutting configuration, in accordance with one embodiment of the present invention.
Figure 2:
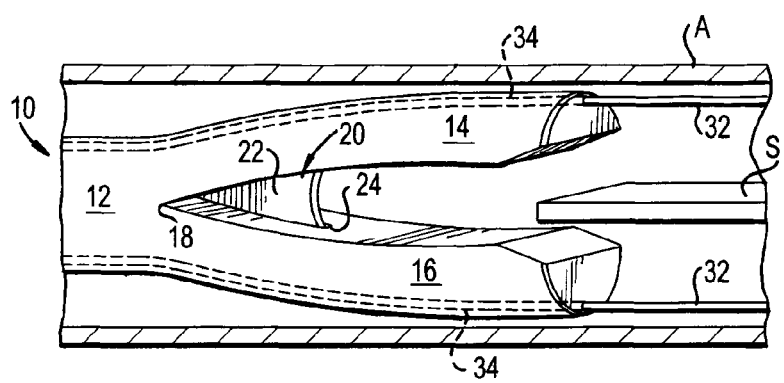
FIG. 2 illustrates a view of the catheter of FIG. 1, still within the blood vessel and traversing guidewires, now with distal arms opening and separated, while guided by the guide wires, providing that a cutting component within the arms receive and engage an edge end of a septum.
Figure 3:
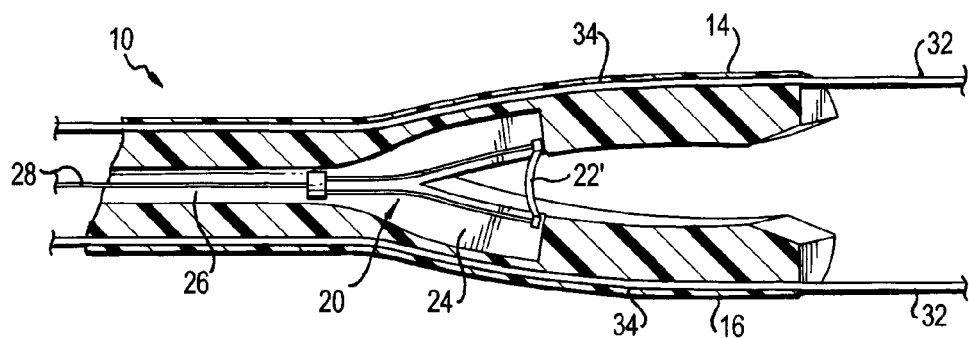
FIG. 3 illustrates a cross-section of one embodiment of the catheter of the present invention, where the cutting component is a RF energized electrode, and further showing internal components and operation of the catheter.
Figure 4:
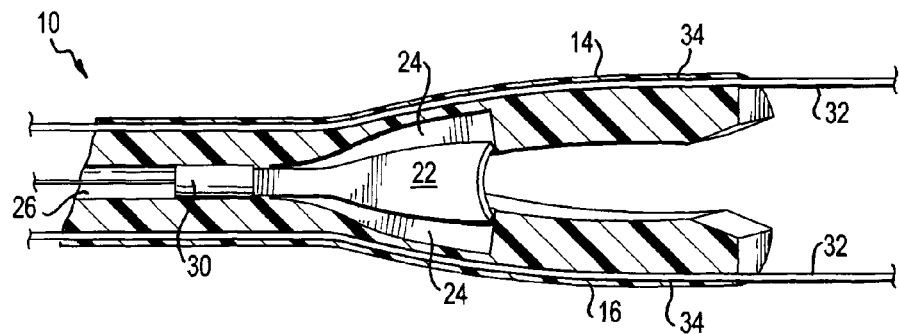
FIG. 4 illustrates a cross-section of another embodiment of the catheter of the present invention, where the cutting component is a ultrasound energized cutting blade, and further showing internal components and operation of the catheter.

FIGS. 1 and 2 show a septotomy catheter 10 within a blood vessel, typically an aorta A. The catheter 10 has a base section 12 from which a pair of flexible arms (or tips) 14, 16 extend. FIG. 1 shows the catheter 10 being advanced in the aorta A in a proximal direction, from a femoral artery toward the heart. FIG. 2 shows the catheter 10 after advancement in the Aorta A and upon separation of the flexible arms 14, 16 resulting in a distal end of the catheter 10 assuming a general Y-shape. FIGS. 3 and 4 illustrate embodiments of the catheter 10 in cross-section, better showing internal components and operation of the catheter.

Located at a vertex 18 of the catheter 10 is a cutting assembly 20, formed at the distal end of the base section 12 and the proximal end of the two arms 14, 16. The cutting assembly 20 is preferably non-mechanically actuated (e.g., not micro-scissors, a moving blade, a jigsaw or serrated wires). A septum cutting component 22 of the cutting assembly 20 spans the vertex 18 of the catheter 10, perpendicular to a longitudinal axis of the catheter 10. Each end of the septum cutting component 22, and also a respective adjacent, longitudinal side of the cutting assembly 20 or cutting component 22, resides inside a notch or trough 24 within each of the two arms 14, 16. The notch 24 provides that the cutting assembly 20, and particularly the end of the septum cutting component 22, are protected by (e.g., completely enclosed within) the notches 24 and by the closure of the two arms 14, 16 (as shown in FIG. 1). When open, the arms 14, 16 receive the septum S and direct the septum S to the cutting component 22. The catheter 10 is snugly configured, with each end of the perpendicularly spanning cutting component 22 nestled within the notch 24 of each arm 14, 16, so that the septum S, if abutting an arm 14, 16, during use, is movably directed along the arm to the cutting component 22. The septum does not snag at the juncture of the cutting component 22 and respective arm 14, 16, due to the direct transition of arm 14, 16 to cutting component 22. Overall, a profile of the closed, cutting end of the catheter 10 (i.e., the distal end of the catheter 10, including the two arms 14, 16 and the vertex 18) has the same profile as the remaining base section 12 of the catheter 10 (as shown in FIG. 1).

In one embodiment, the cutting assembly 20 is radio-frequency (RF) energized, and the septum cutting component 22 is an electrode. The electrode can be a wire, bar, rod, sheet, blade or plate. If a conductive sheet or plate, much of the sheet or plate can be insulated (except for a most distal portion thereof). A remaining, uninsulated portion of the electrode would likely resemble a wire, bar or rod spanning the vertex 18 of the catheter 10, perpendicular to the longitudinal axis of the catheter 10. In this instance, longitudinal sides of the sheet or plate would reside inside the notch or trough 24 within each of the two arms 14, 16.

The RF energization can be monopolar or bipolar. In monopolar use, the active electrode 22 is placed at the cutting site, and a return electrode pad is attached to the patient (not shown). High frequency electrical current flows from a generator (not shown), to the electrode 22, through to target tissue, to the patient return pad, and back to the generator. The catheter 10 includes a central lumen 26 for the traversing therethrough of a RF current wire 28 (as shown in FIG. 3). In a bipolar embodiment, usually lower voltages are employed, thereby less energy is required. A return electrode or pad must therefore be much closer to the active electrode, and to the cutting site. RF current is restricted to tissue between the active and return electrodes, thereby giving better control over the targeted area and preventing possible current damage to surrounding sensitive tissue.

In another embodiment, the cutting assembly 20 employs an ultrasonic static motor 30 and the septum cutting component 22 is an ultrasonic cutting blade (as shown in FIG. 4). The ultrasonic motor 30 can take the form of a piezoelectric device (ceramic PTZ disks) connected to cutting component 22, energized through a thin conductor (wire) imbedded in the catheter that delivers electric current. The ultrasonic motor 30 is preferably housed within base section 2. The ultrasonic static motor transforms electrical voltage into high-frequency (approximately 50,000 Hertz) vibration, and the vibration is transmitted to the cutting component 22 and causes the blade to cut through the septum on contact.

In still another embodiment, the cutting assembly 20 employs an excimer laser (or exciplex laser), where the septum cutting component 22 is the generated laser light in the ultraviolet range (not shown). The excimer laser fiber travels through the central lumen 26 of the catheter 10. The high-power ultraviolet output of excimer lasers are useful and efficient for delicate surgeries, as the laser can make clean, precise cuts in tissue.

As better illustrated in FIGS. 3 and 4, but also shown in FIGS. 1 and 2, a pair of guide wires 32 traverse the catheter 10 through channels 34, one guide wire 32 per channel 34. Each guide wire 32 passes through a respective channel 34 in the base section 12 and then separate, with one guide wire 32 traversing through one channel 34 in each of the arms 14, 16. Preferably, the guide wires 32 traverse channels 34 of the catheter 10 linearly, proximally to distally (relative to the catheter) in a single direction (i.e., no looping or doubling back).

Figure 5:
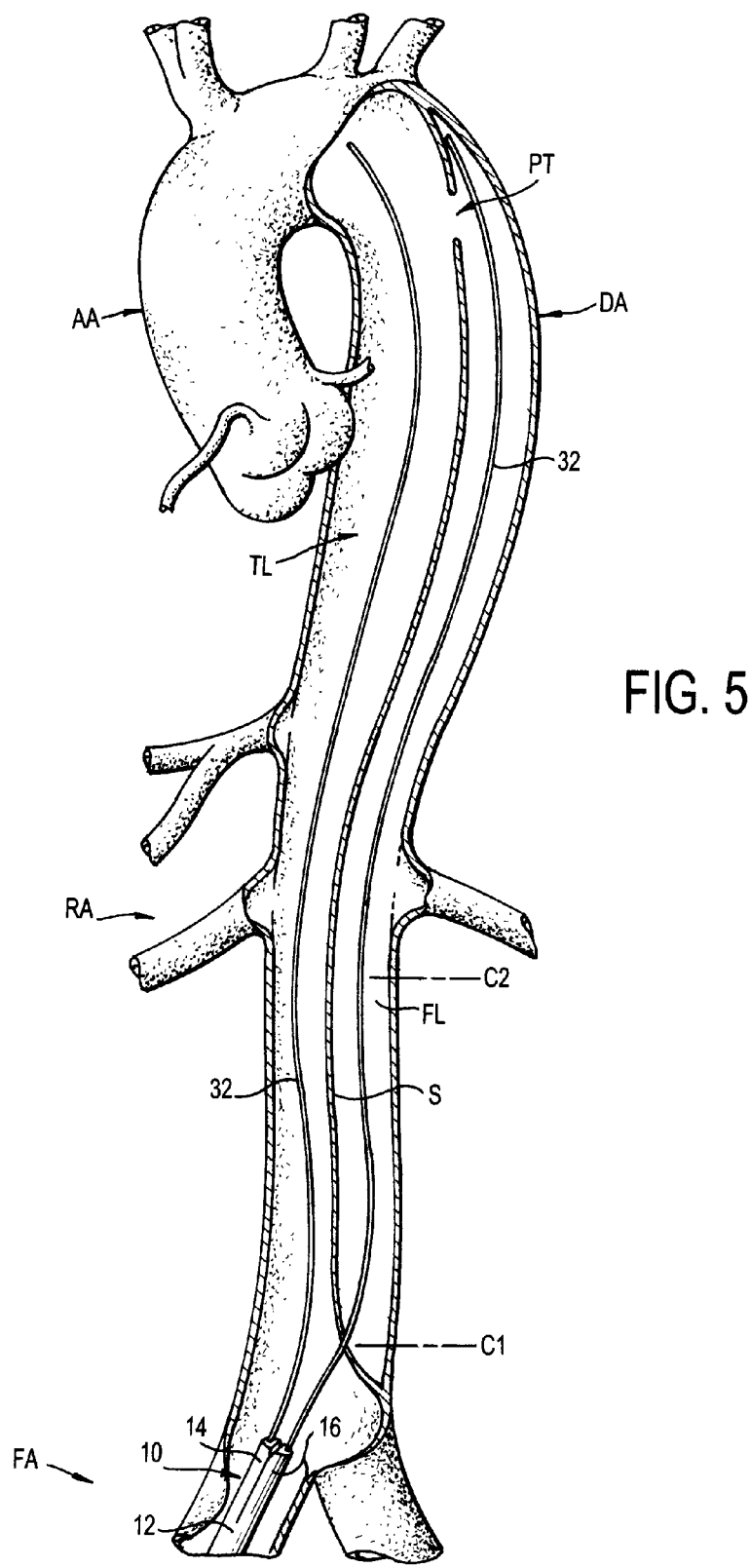
FIG. 5 illustrates a cross-section of a Type B aortic dissection, showing guide wire insertion (one guide wire in a true lumen and one guide wire in a false lumen), with an embodiment of the catheter of the present invention traversing over the guidewires, the catheter shown in a closed, non-cutting configuration.
Figure 6:
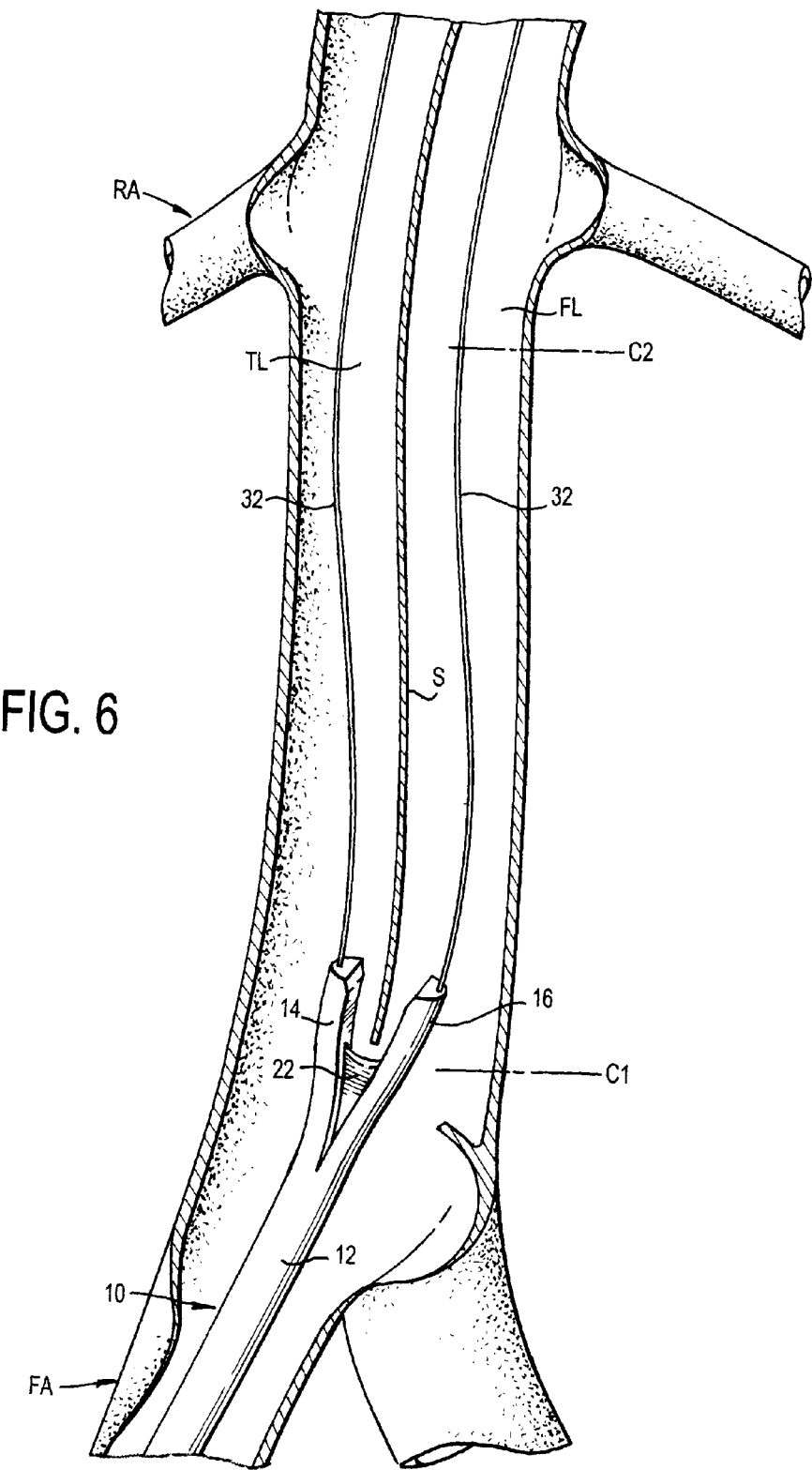
FIG. 6 illustrates a cross-section of a Type B aortic dissection, again showing guide wires inserted, with an embodiment of the catheter of the present invention tracking the guidewires, the catheter now with distal arms separated, while guided by the guide wires, revealing a cutting component therein, the arms receiving for cutting a septum of the aortic dissection.

FIGS. 5 and 6 illustrate a cross-section of a Type B aortic dissection, a method of treating aortic dissection, a method for septum cutting, and for use of the catheter 10. Shown are an ascending aorta AA, descending aorta DA, femoral artery FA, renal arteries RA, septum S, proximal tear PT, true lumen TL, and false lumen FL. When referring to the aortic dissection, the septum S thereof, and surgical activity involving the septum S, an end of the dissection closest to the heart is referred to as the proximal end, and an end furthest from the heart is referred to as the distal end (bottom of page).

Now referring to FIGS. 5 and 6, the guide wires 32 are first inserted into the blood vessel, at the femoral artery, and advanced in a proximal direction, along the aorta A, toward a point of aortic dissection. Since the guide wires 32 are constrained by the blood vessel walls A, the guide wires 32 are roughly parallel to each other, and parallel to the axis of the blood vessel. Upon reaching a point of aortic dissection, one guide wire 32 is inserted (penetrated) through a septum S of the aortic dissection, into a false lumen FL thereof. The other guide wire 32 is equally advanced, but remains in a true lumen TL of the aorta (alongside the dissection).

Thus, both guide wires 32 have entered the femoral artery FA through the same puncture or through an introducer sheath inserted into the artery. Both guidewires 32 are fully advanced within the aorta A to a final location, with one guide wire 32 inserted through the septum S into the false lumen FL and one guide wire 32 in the true lumen TL. A final location of the guide wires 32 extend beyond a point where a cutting of the septum will cease (with one guide wire 32 on each side of the septum S along the dissection). The proximal ends of the guidewires 32, remaining outside the body, are then fed into the channel(s) 34 at a distal end of the catheter 10. The catheter 10 is inserted in the sheath and pushed along the vessel, tracking and moving along (over) the guide wires 32, as the guide wires 32 pass through the channels 34. As the catheter 10 is advanced within the aorta A, along the parallel guide wires 18, prior to reaching the aortic dissection, the catheter 10 remains in a closed, non-cutting configuration, with cutting component 22 non-exposed (as shown in FIGS. 1 and 5). Shortly, the catheter 10 approaches a distal end of the septum S of the aortic dissection, at the point where one guide wire 18 penetrates through the septum S.

The arms 14, 16 of the catheter 10 do not diverge into a Y-shape (and thus revealing the cutting component 22) until the guide wires 32 separate at the lower edge (distal end) of the septum S (at the point where one guide wire 18 penetrates through the septum S) As shown in FIG. 6, the catheter 10 tracks the guide wires 32, the arms 14, 16 separate, forming a Y-shape, with one arm 14 disposed in the true lumen TL and another arm 16 disposed in the false lumen FL. The septum S is now located between the arms 14, 16, and is directed by the arms 14, 16 into the cutting component 22 while the catheter 10 is continually advanced toward the heart (in a proximal direction relative to the dissection).

Referring to FIG. 6, as the catheter 10 continues proximal advancement (by continually tracking the guide wires 32 previously placed in the aorta A), the cutting component 22 proximally moves and cuts along the length of septum S. The catheter 10 follows the guide wires 32, thereby directing the path (and the opening and closing) of the arms 14, 16. When open, the arms 14, 16 receive the septum S and direct the septum S to the cutting component 22. In all embodiments, the catheter 10 is snugly configured, with each end of the cutting component 22 nestled within the notch 24 of each arm 14, 16, so that the septum S, if abutting an arm 14, 16, is movably directed along the arm to the cutting component 22. The septum does not snag at the juncture of the cutting component 22 and respective arm 14, 16.

As noted, acute aortic dissections often require only a few centimeters of septum division to equalize pressure between the lumens, and to provide low resistance outflow of both lumens to avoid development of aneurysmal dilatation of the false lumen (e.g., 5-15 cm in the instance of cutting from the level of the aortic bifurcation to below the renal arteries). FIGS. 5 and 6 illustrate an instance of aortic dissection where guide wire 32 penetration of the septum S occurs, generally, at the femoral or external iliac level C1 (i.e., cutting start point C1). Cutting of the septum S begins at point C1 and ceases below the renal arteries RA, at C2 (i.e., cutting end point C2). In chronic dissections, where different viscera may be perfused by either lumen, septum cutting is needed to convert the double lumen into a single one, and cutting the fibrous septum may be required to the proximal tear PT.

After a suitable length of septum S cutting is complete, the cutting component is de-energized, and the catheter 10 is withdrawn, in a distal direction, from the blood vessel. Any remaining septum S is undisturbed. As noted, the methods and device of the present invention teach septum S cutting in a retrograde manner (from distal to proximal along the aortic dissection), which is the only safe, effective way to divide the septum S. Dividing a septum from a proximal to distal point, by pulling or retraction of a catheter device, may result in sudden collapse of the true lumen, sometimes with catastrophic consequences.

FIG. 7 illustrates an alternative embodiment of the catheter 10, where each of the guide wires 32 extend and traverse through a longitudinal channel 34 residing only in a respective arm 14, 16. To better illustrate this alternative feature, and other features within the arms 14, 16, FIG. 7 is provides see-through capability of the arms 14, 16 of the catheter 10.

In the FIG. 7 embodiment, each channel 34 (and therefore each guide wire 32 during catheter use) exits the respective arm 14, 16 at a proximal end 36 thereof, in a vicinity of the cutting component 22. The guide wires 32 are thereafter located exterior to the catheter 10, alongside and parallel to the base section 2. The channel 34 of this alternative embodiment may exit the proximal end 36 of the arm 14, 16 at a location longitudinally distal to the cutting component 22, longitudinally proximal to the cutting component 22, and/or at an angle relative to the longitudinal axis of the catheter 10, to ensure that the catheter 10, when in a closed, non-cutting configuration (with cutting component 22 non-exposed), has arms 14, 16 completely abutting one another (similar to that shown in FIG. 1).

FIG. 7 also illustrates respective notches 24 in each arm 14, 16 of the catheter 10, showing well-defined longitudinal wells or troughs that house a respective end of each cutting component 22, and that house respective sides of each cutting component 22 (or that house insulated portions of the cutting component, or that house and insulate wires feeding an electrode cutting component 22, all comprised within the cutting assembly 20).

FIG. 8 illustrates another alternative feature of the catheter 10. A distal end of the catheter 10 can include one or more flexible wings 40, preferably small, on an outer aspect of the base section 12, proximal to the cutting assembly 20, to better align the catheter 10, and the cutting component 22, within the aorta A and toward a center axis of the septum S. Further, and preferably smaller, flexible wings 40 could extend from the arms 14, 16. The flexible wings 40 may have a fixed shape, or may be collapsible, providing that the wings 40 can be carried on or inside the catheter 10 until the diameter of the lumen into which the catheter 10 is advanced permits its passive extending (or un-flexing). The flexible wings 40, illustrated in FIG. 8, form of a loop made of the material similar to that of the catheter 10. This alternative feature can be used when the catheter 10 is introduced into the blood vessel by insertion through a hollow outer catheter, introducer element, or similar body. In this instance, when the catheter 10 protrudes from the introducer element, the flexible wings 40 expand (open or axially extend). When the catheter 10 is withdrawn from the blood vessel, back into the introducer element, the wings 40 would fold forward onto the outer walls of the base section 12 or the arms 14, 16.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, features detailed as included in certain specific embodiments above are recognized as interchangeable and possibly included in other detailed embodiments. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:
1. A septotomy catheter, comprising:
a base section having a central lumen therethrough;
two flexible arms extending from a distal end of the base section, each arm having a channel therethrough for a passage of a guide wire, wherein:
with distal ends of the two flexible arms separated, the two arms form a Y-shape with the base section;
with distal ends of the two flexible arms together, the two arms have a longitudinal profile, about a periphery thereof, identical to a longitudinal profile of the base section;
a cutting component residing between the two arms adjacent to the distal end of the base section, wherein:
the cutting component faces distally and spans the two flexible arms when separated, residing perpendicularly to a longitudinal axis of the catheter;

the two arms each further comprise a notch therein, each notch housing a respective end of the cutting component, each notch providing that the respective end of the cutting component is not exposed outside the catheter when the two arms are separated;

the two arms, with distal ends together, completely house the cutting component therein, whereby no part of the cutting component is exposed outside the catheter.

2. The catheter of claim 1, wherein the cutting component is non-mechanically actuated or energized.

3. The catheter of claim 1, wherein the cutting component is an electrode energized by radio-frequency (RF) current.

4. The catheter of claim 3, wherein the electrode is a wire.

5. The catheter of claim 3, wherein the electrode is a flat plate or blade, entirely insulated except for a most distal portion thereof which is uninsulated, the uninsulated portion resembling a wire or rod spanning the two flexible arms when separated, residing perpendicularly to the longitudinal axis of the catheter.

6. The catheter of claim 5, wherein longitudinal, insulated sides of the flate plate or blade reside inside respective notches of the two arms.

7. The catheter of claim 3, wherein the radio-frequency (RF) current is provided by a wire residing within the central lumen of the base section.

8. The catheter of claim 3, wherein the RF energization is monopolar.

9. The catheter of claim 3, wherein the RF energization is bipolar.

10. The catheter of claim 1, wherein the cutting component is an ultrasonic cutting blade, having a cutting edge facing distally and spanning the two flexible arms when the arms are separated.

11. The catheter of claim 10, further comprising an ultrasonic static motor residing within the base section, along the central lumen thereof.

12. The catheter of claim 1, further comprising two base section channels extending through an entirety of the base section, the base section channels being parallel to the central lumen, wherein each base section channel communicates with a respective channel of the arm to provide passage of two guide wires, one guide wire per channel, through an entirety of the catheter.

13. The catheter of claim 1, wherein the cutting component is an excimer laser.

14. A septotomy catheter, comprising:
a base section having a central lumen therethrough;
two flexible arms extending from a distal end of the base section, each arm having a channel therethrough for a passage of a guide wire, wherein:
with distal ends of the two flexible arms separated, the two arms form a Y-shape with the base section;
with distal ends of the two flexible arms together, the two arms have a longitudinal profile, about a periphery thereof, identical to a longitudinal profile of the base section; and
a non-mechanically actuated cutting component residing between the two arms in a vicinity of the distal end of the base section, wherein the cutting component is an electrode spanning between the two flexible arms when separated, residing perpendicularly to a longitudinal axis of the catheter;
wherein the two arms each further comprise a notch therein, and the two arms, with distal ends together, completely house the electrode within the notches, whereby no part of the electrode is exposed outside the catheter.

15. The catheter of claim 14, wherein each notch houses a respective end of the electrode, each notch providing that the respective end of the electrode is not exposed outside the catheter when the two arms are separated.

16. The catheter of claim 14, wherein the electrode is energized by radio-frequency (RF) current.

17. The catheter of claim 14, further comprising one or more flexible wings axially expandable and collapsible from an outer aspect of the catheter, wherein the one or more wings are carried in a collapsed state until a diameter of a vessel into which the catheter is advanced permits passive expansion against inner walls of the vessel, whereby the wings align the catheter and the cutting component within the vessel.

18. A method of treating an aortic dissection, comprising the steps of:
providing or receiving the septotomy catheter of claim 1;
inserting two guide wires into an arterial system;
moving the two guide wires proximally, into a descending aorta, wherein the guide wires are substantially parallel to one another and spaced apart a distance;
penetrating a septum of the aortic dissection, into a false lumen thereof, distal of a proximal tear of the aortic dissection, at a certain location, with a first of the two guide wires, wherein the guide wires become more separated from one another at the certain location of septum penetration;
continuing to move the guide wires proximally, toward the proximal tear, with the first guide wire in the false lumen and a second guide wire in a true lumen of the aortic dissection, with septum of the aortic dissection between the two guide wires, wherein the guide wires remain spaced apart, proximal of the certain location of septum penetration, at least the distance or greater;
inserting a distal end of the septotomy catheter over the guide wires, one guide wire in each of the two channels of the septotomy catheter;
moving the septotomy catheter proximally in the arterial system, with guide wires passing therethrough, toward the aortic dissection, the septotomy catheter tracking the substantially parallel guide wires and remaining closed, with the distal ends of the arms together, completely housing the cutting component therein, whereby no part of the cutting component is exposed outside the catheter;
penetrating the septum of the aortic dissection, into the false lumen thereof, at the certain location, with one of the flexible arms, while the one of the flexible arms tracks the first guide wire into the false lumen and then proximally thereof, the other of the flexible arms tracking the second guide wire proximally in the true lumen, wherein the distal ends of the two flexible arms separate, forming a Y-shape with the base section to expose the cutting component outside the catheter, from between the flexible arms, with the cutting component facing distally relative to the catheter; and
moving the septotomy catheter further proximally, with arms separated, the septotomy catheter receiving the septum between the separated arms, where the separated arms, with catheter moving proximally, direct a distal end of the penetrated septum into the cutting component, whereby the septum is cut a desired distance determined by further proximal movement of the catheter.

19. The method of claim 18, wherein the cutting component is energized only upon receipt of the septum between the separated arms, with septum in close proximity to the cutting component.

20. A method of treating an aortic dissection, comprising the steps of:
providing or receiving the septotomy catheter of claim 14;
inserting two guide wires into an arterial system;
moving the two guide wires proximally, into a descending aorta, wherein the guide wires are substantially parallel to one another and spaced apart a distance;
penetrating a septum of the aortic dissection, into a false lumen thereof, distal of a proximal tear of the aortic dissection, at a certain location, with a first of the two guide wires, wherein the guide wires become more separated from one another at the certain location of septum penetration;
continuing to move the guide wires proximally, toward the proximal tear, with the first guide wire in the false lumen and a second guide wire in a true lumen of the aortic dissection, with septum of the aortic dissection between the two guide wires, wherein the guide wires remain spaced apart, proximal of the certain location of septum penetration, at least the distance or greater;
inserting a distal end of the septotomy catheter over the guide wires, one guide wire in each of the two channels of the septotomy catheter;
moving the septotomy catheter proximally in the arterial system, with guide wires passing therethrough, toward the aortic dissection, the septotomy catheter tracking the substantially parallel guide wires and remaining closed, with the distal ends of the arms together, completely housing the cutting component therein, whereby no part of the cutting component is exposed outside the catheter;
penetrating the septum of the aortic dissection, into the false lumen thereof, at the certain location, with one of the flexible arms, while the one of the flexible arms tracks the first guide wire into the false lumen and then proximally thereof, the other of the flexible arms tracking the second guide wire proximally in the true lumen, wherein the distal ends of the two flexible arms separate, forming a Y-shape with the base section to expose the cutting component outside the catheter, from between the flexible arms, with the cutting component facing distally relative to the catheter; and
moving the septotomy catheter further proximally, with arms separated, the septotomy catheter receiving the septum between the separated arms, where the separated arms, with catheter moving proximally, direct a distal end of the penetrated septum into the cutting component, whereby the septum is cut a desired distance determined by further proximal movement of the catheter.

* * * * *

UNITED STATES PATENT AND TRADEMARK OFFICE
CERTIFICATE OF CORRECTION

PATENT NO. : 9,681,915 B2  
APPLICATION NO. : 15/131504  
DATED : June 20, 2017  
INVENTOR(S) : Ramon Berguer, Juan Parodi and Gene Parunak Page 1 of 1

It is certified that error appears in the above-identified patent and that said Letters Patent is hereby corrected as shown below:

On the Title Page

Item (72), add the following inventor:
-- Gene Parunak, Saline, MI (US) --

Signed and Sealed this  
Tenth Day of December, 2019

Andrei Iancu  
*Director of the United States Patent and Trademark Office*